(12) United States Patent  
Chen et al.

(10) Patent No.: US 7,595,419 B2
(45) Date of Patent: Sep. 29, 2009

(54) PROCESS AND INTERMEDIATES FOR THE PREPARATION OF 3-(AMINO)-3-CYCLOBUTYLMETHYL-2-HYDROXY-PROPIONAMIDE OR SALTS THEREOF

(75) Inventors: Minzhang Chen, Plainsboro, NJ (US); Michael D. Green, Willingboro, NJ (US); Fucheng Zhang, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/236,447

(22) Filed: Sep. 27, 2005

(65) Prior Publication Data

US 2006/0030734 A1    Feb. 9, 2006

Related U.S. Application Data

(62) Division of application No. 10/867,601, filed on Jun. 15, 2004, now Pat. No. 6,992,220.

(60) Provisional application No. 60/479,487, filed on Jun. 17, 2003.

(51) Int. Cl.
*C07C 271/14* (2006.01)

(52) U.S. Cl. .................................................. 560/115

(58) Field of Classification Search ................. 560/115
See application file for complete search history.

(56) References Cited

U.S. PATENT DOCUMENTS

2003/0207861 A1    11/2003    Arasappan et al.
2004/0254117 A9    12/2004    Saksena et al.

FOREIGN PATENT DOCUMENTS

WO    WO 02/08244      1/2002
WO    WO 03/062265     7/2003

*Primary Examiner*—Shailendra Kumar
(74) *Attorney, Agent, or Firm*—Patent Practitioners of Schering Corporation

(57) ABSTRACT

In one embodiment, the present application relates to a process of making a compound of formula I:

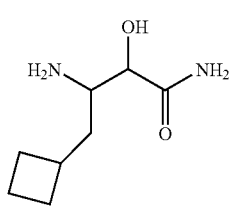

and to certain intermediate compounds that are made within the process of making the compound of formula I.

3 Claims, No Drawings

US 7,595,419 B2

PROCESS AND INTERMEDIATES FOR THE PREPARATION OF 3-(AMINO)-3-CYCLOBUTYLMETHYL-2-HYDROXY-PROPIONAMIDE OR SALTS THEREOF

RELATED APPLICATIONS

This application is a divisional of application U.S. Ser. No. 10/867,601, filed Jun. 15, 2004, now U.S. Pat. No. 6,992,220, and herein incorporated by reference, which in turn claims benefit under 35 USC 119(e) to provisional application U.S. Ser. No. 60/479,487, filed Jun. 17, 2003.

FIELD OF THE INVENTION

This invention relates to the process and intermediates for the preparation of 3-(amino)-3-cyclobutylmethyl-2-hydroxy-propionamide or salts thereof having the following structure (formula I):

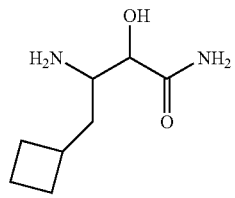

or salts thereof.

BACKGROUND OF THE INVENTION 3-(Amino)-3-cyclobutylmethyl-2-hydroxy-propionamide is disclosed in U.S. patent application Ser. Nos. 09/908,955 which was filed Jul. 19, 2001, and Ser. No. 10/052,386 which was filed Jan. 18, 2002, which are each incorporated herein by reference.

The compound of formula I is a key intermediate used in the preparation of the hepatitis C virus ("HCV") protease inhibitor (1R,2S,5S)-3-azabicyclo[3,1,0]hexane-2-carboxamide, N-[3-amino-1-(cyclobutylmethyl)-2,3-dioxopropyl]-3-[(2S)-2-[[[1,1-dimethylethyl)amino]carbonylamino]-3,3-dimethyl-1-oxobutyl]-6,6-dimethyl having the following structure:

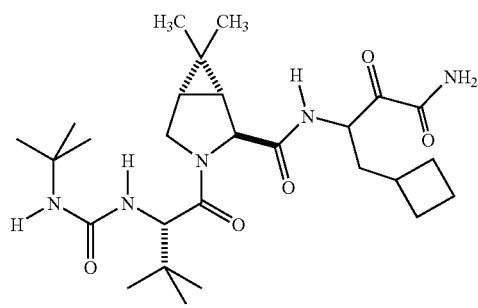

The compound of formula Z disclosed in the above-noted patent applications is useful for treating hepatitis C and related disorders. Specifically, the compound of formula Z is an inhibitor of the HCV NS3/NS4a serine protease.

There remains a need for methods of synthesizing compounds useful in the treatment or prevention or amelioration of one or more symptoms of hepatitis C.

In view of the importance of hepatitis C virus ("HCV") protease inhibitors, new, novel methods of making such antagonists are always of interest.

SUMMARY OF THE INVENTION

In one embodiment, the present application relates to a process of making a compound of formula I:

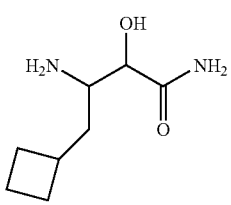

or salts thereof.

The invention also relates to certain intermediate compounds that are made within the process of making the compound of formula I.

The process of making the compound of formula I comprises:

(1) alkylating and deprotecting a compound of formula II to yield a compound of formula III:

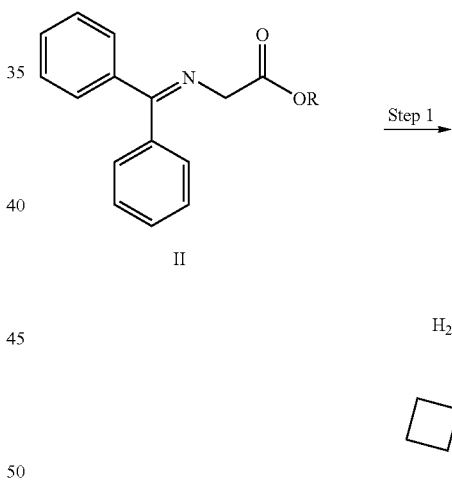

wherein R represents an alkyl group or substituted alkyl group;

(2) protecting the compound of formula III with protecting group (P) to yield a compound of formula IV:

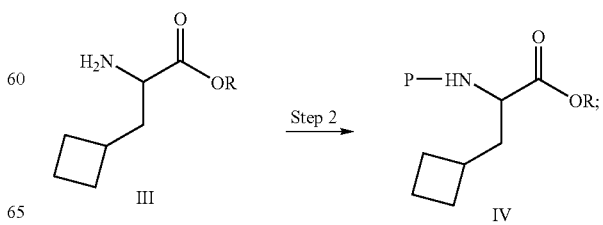

(3) reducing the compound of formula IV to yield a compound of formula V:

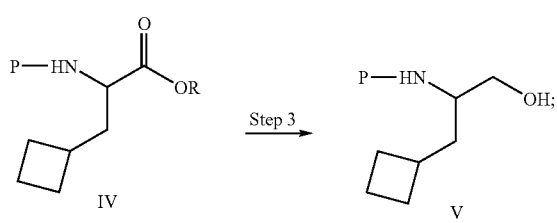

(4) oxidizing the compound of formula V to yield a compound of formula VI:

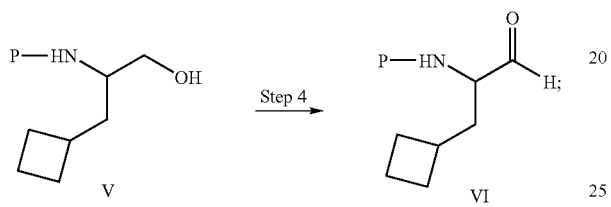

(5) reacting the compound of formula VI with

to yield a compound of formula VII:

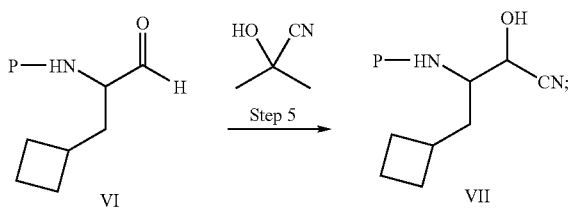

(6) hydrating the compound of formula VII to yield a compound of formula VIII:

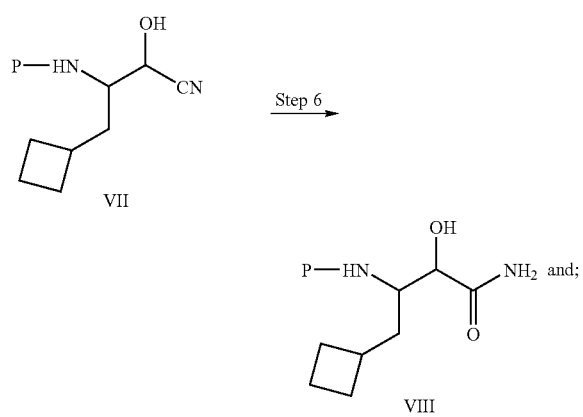

(7) deprotecting the compound of formula VIII to yield the compound of formula I:

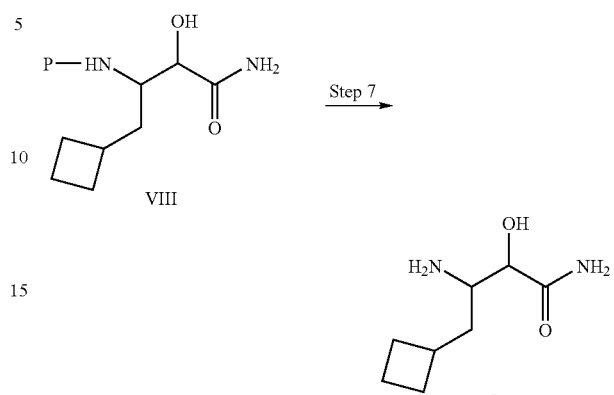

or salts thereof.

The inventive process to make the compound of formula I has several advantages: It is more suitable for scale up for manufacture, and it is more cost effective.

DESCRIPTION OF THE INVENTION

As used above, and throughout the specification, the following terms, unless otherwise indicated, shall be understood to have the following meanings:

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, cyano, hydroxy, alkoxy, alkylthio, amino, —NH(alkyl), —N(alkyl)$_2$, carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, and trifluoromethyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Non-limiting examples of suitable solvates include ethanolates, methanolates, and the like. "Hydrate" is a solvate wherein the solvent molecule is H₂O.

In one embodiment, the present invention relates to a process for preparing the compound of formula I. The inventive process is schematically described in Scheme I below:

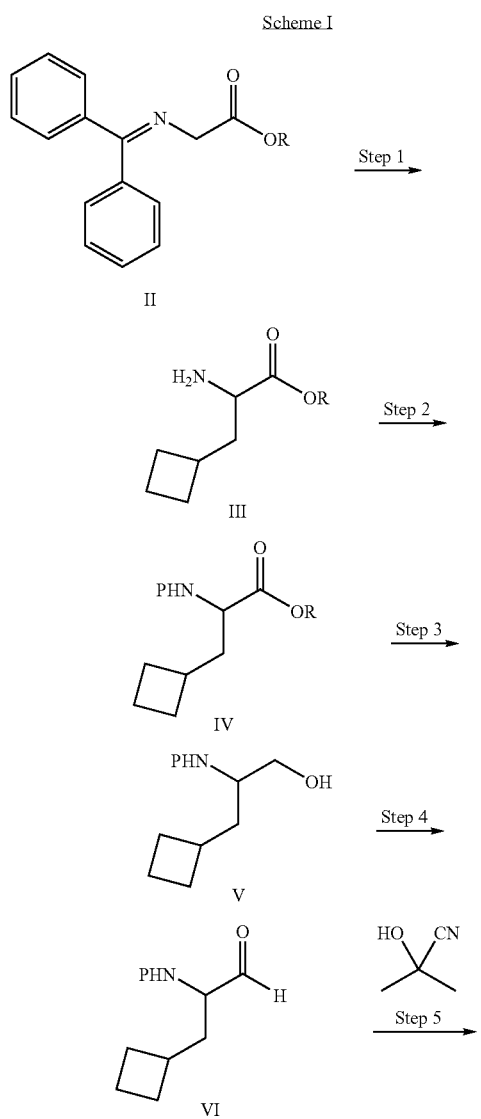

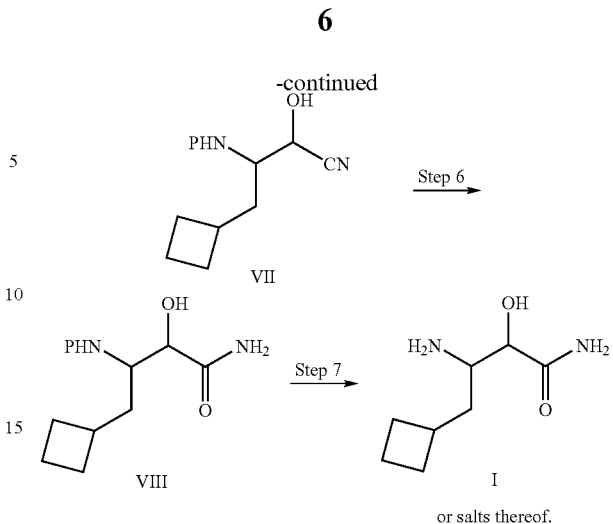

or salts thereof.

R represents an alkyl or substituted alkyl group. Non-limiting examples of alkyl groups are $(C_1-C_{12})$alkyl, $(C_1-C_6)$alkyl, and $(C_1-C_3)$alkyl.

P is a protecting group. Examples of N-protecting groups suitable in the practice of the invention include allyl, methoxymethyl, benzyloxymethyl, $CY_3CO$ (where Y is a halogen), benzyloxycarbonyl, trityl, pivaloyloxymethyl, tetrahydranyl, benzyl, di(p-methoxyphenyl)methyl, triphenylmethyl, (p-methoxyphenyl)diphenylmethyl, diphenylphosphinyl, benzenesulfenyl, methylcarbamate, 2-trimethylsilylethyl carbamate, 1-methyl-1-phenylethyl carbamate, t-butyl carbamate ("t-Boc"), cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate and S-benzylcarbamate.

Preferred N-protecting groups include methylcarbamate, 2-trimethylsilylethyl carbamate, 1-methyl-1-phenylethyl carbamate, t-butyl carbamate ("t-Boc"), cyclobutyl carbamate, 1-methylcyclobutyl carbamate, adamantyl carbamate, vinyl carbamate, allyl carbamate, cinnamyl carbamate, 8-quinolyl carbamate, benzyl carbamate, 9-anthrylmethyl carbamate, diphenylmethyl carbamate, S-benzylcarbamate, more preferably t-Boc.

Step 1:

To a solution of 35.0 kg (131 mol) of a compound of formula II in a suitable solvent at a temperature ranging from about −20° C. to about 70° C., preferably from about 0° C. to about 50° C., more preferably from about 20° C. to about 30° C., is added suitable base. Non-limiting examples of suitable bases that can be used include metal hydrides, alkyl lithium and metal alkoxides. Preferred bases are metal alkoxides. The metal in either the metal alkoxide or the metal hydride can be sodium, potassium, and the like. The alkoxide can contain from 1 to 12 carbon atoms, preferably from 1 to 6 carbon atoms, more preferably from 1 to 4 carbon atoms. An example of a preferred metal alkoxide includes potassium tert-butoxide. Examples of alkyl lithium bases include lithium diethylpropylamide and butyl lithium. Non-limiting examples of the suitable solvents include, aromatic solvents, hydrocarbon solvents and ether solvents. Non-limiting examples of aromatic solvents include benzene, xylene, and toluene. Non-limiting examples of hydrocarbon solvents include pentane, hexane and heptane. Non-limiting examples of ether solvents include THF, TBME, and diethylether. Preferred solvents are ether solvents such as THF, TBME, and diethylether, more preferably THF. The mixture is then agitated for about 1 hour or until the reaction is complete at a temperature ranging from about −45° C. to about 40° C., preferably from about −25° C. to about 20° C., more preferably from about −5° C. to about 0° C. (Halomethyl)cyclobutane or (sulfonatemethyl)cyclobutane is then added, preferably(halomethyl)cyclobutane), more preferably (bromomethyl)cyclobutane. The (halomethyl)cyclobutane can be used generally from about 0.2 to about 10 molar equivalents with respect to the compound of formula II, preferably from about 1 to about 5 molar equivalents, and more preferably from about 1 to about 1.5 molar equivalents. Any excess of (halomethyl)cyclobutane can be used. The mixture is then agitated for 24 hours or until the reaction is complete at a temperature ranging from about −20° C. to about 65° C., preferably from about 0° C. to about 45° C., more preferably from about 20° C. to about 25° C. After this period of time, an aqueous solution of acid is added. Non-limiting examples of acids that can be added include inorganic or organic acids such as ammonium sulfate, ammonium nitrate, ammonium chloride, $H_2SO_4$, HCl, $H_3PO_4$, citric acid, mesyl chloride, paratoluenesulfonic acid, paratoluenesulfonic acid pyridinium salt, alkylsulfonic acid, and the like, or mixtures thereof. Preferred acids are inorganic acids such as $H_2SO_4$, HCl, and $H_3PO_4$, preferably HCL. The resulting mixture was agitated for 2 hours or until the reaction is complete to provide a compound of formula III.

Step 2:

An N-protecting group (P) in a suitable solvent (24.9 kg, 131 mol) is added to the compound of formula III from step 1. The N-protecting group can be used generally from about 0.2 to about 10 molar equivalent with respect to the compound of formula III, preferably from about 1 to about 5 molar equivalents, and more preferably from about 1 to about 1.5 molar equivalents. Non-limiting examples of the suitable solvents that can be used in step 2 include aromatic solvents, hydrocarbon solvents and ether solvents. Preferred solvents are ether solvents such as THF, TBME, and diethylether, more preferably THF.

After the addition, the reaction mixture is adjusted to a temperature ranging from about −20° C. to about 65° C., preferably from about 0° C. to about 45° C., more preferably from about 20° C. to about 25° C. and agitated for about 4 hours or until the reaction is complete to yield a compound of formula IV.

Step 3:

A solution of a reducing agent in a suitable solvent is added to the compound of formula IV from step 2. Non-limiting examples of reducing agents include metal hydrides such as lithium aluminum hydride ($LiAlH_4$), lithium borohydride ($LiBH_4$) or sodium borohydride ($NaBH_4$). The reducing agent can be used generally from about 0.1 to about 10 molar equivalents with respect to the compound of formula IV, preferably from about 0.25 to about 5 molar equivalents, and more preferably from about 1 to about 2 molar equivalents. Any excess of reducing agent can be used. Non-limiting examples of suitable solvents that can be used in step 3 include aromatic solvents, hydrocarbon solvents and ether solvents. Preferred solvents are ether solvents such as THF, TBME, and diethylether, more preferably THF. The resulting mixture is agitated for about 6 hours or until the reaction is complete to yield a compound of formula V.

Step 4:

To the compound of formula V from step 3 in a suitable solvent is slowly added an oxidizing agent capable of oxidizing the alcohol group of formula V into an aldehyde group. Preferably, one or more catalysts and a base is added prior to the oxidizing agent. A preferred combination of catalysts, base and oxidizing agent includes 2,2,6,6-Tetramethyl-1-piperidinyloxy (TEMPO) and a metal bromide each as catalysts, wherein the metal of the metal bromide can be Na, K, Li and the like, sodium bicarbonate as the base, and sodium hypochlorite as the oxidizing agent. The oxidizing agent can be used generally from about 0.2 to about 10 molar equivalents with respect to the compound of formula V, preferably from about 1 to about 5 molar equivalents, and more preferably from about 1 to about 1.5 molar equivalents. Non-limiting examples of suitable solvents include hydrocarbon solvents, ester solvents, aromatic solvents, THF, and the like, or mixtures thereof. Preferred solvents include the ester solvents, more preferably isopropyl acetate or ethyl acetate. The reaction mixture is stirred for about 30 minutes or until the reaction is complete to yield a compound of formula VI.

Step 5:

To the compound of formula VI from step 4 is added a phase transfer catalyst and a cyanide catalyst such as potassium cyanide, sodium cyanide and the like. Non limiting examples of phase transfer catalysts include tetrabutyl ammonium iodide, tetrabutyl ammonium bromide, methyl tricapryl ammonium chloride, triethyl benzyl ammonium chloride, tetrabutyl ammonium hydrogen sulfate, methyl tributyl ammonium chloride, tetraphenyl phosphonium bromide, tetrabutyl phosphonium bromide, PEG-500 demethyl ether, butyl diglyme, and dibenzo-18-crown-6. Acetone cyanhydrin is added at a temperature ranging from about −25° C. to about 60° C., preferably from about −5° C. to about 40° C., more preferably from about 15° C. to about 20° C. The acetone cyanohydrin can be used generally from about 0.2 to about 10 molar equivalents with respect to the compound of formula VI, preferably from about 1 to about 5 molar equivalents, and more preferably from about 1 to about 1.5 molar equivalents. The mixture is stirred for about 2 hours or until the reaction is complete to yield a compound of formula VIII.

Step 6:

A base in an appropriate solvent and DMSO is added to the compound of formula VII from step 5. An example of an appropriate solvent includes acetone. Non-limiting Examples of appropriate bases include $KCO_3$ or $NaCO_3$. The reaction mixture is heated to a temperature ranging from about 25° C. to about 105° C., preferably from about 45° C. to about 85° C., more preferably from about 60° C. to about 70° C. Hydrogen peroxide is then slowly added to the reaction mixture to yield a compound of formula VIII. Other methods of hydration can be used to convert the compound of formula VII to the compound of formula VIII such as the use of $MnO_4$, or an enzyme that catalyzes hydration.

Step 7:

To the compound of formula VIII from step 6 in a suitable solvent is added an acid. Non-limiting examples of acids that can be added include inorganic or organic acids such as ammonium sulfate, ammonium nitrate, ammonium chloride, trifluoroacetic acid (TFA), $H_2SO_4$, HCl, $H_3PO_4$, citric acid, mesyl chloride, paratoluenesulfonic acid, paratoluenesulfonic acid pyridinium salt, alkylsulfonic acid, and the like, or mixtures thereof. Preferred acids include TFA, $H_2SO_4$, HCl, and $H_3PO_4$, more preferably TFA or HCl. After the addition of acid, the mixture is heated to a temperature ranging from about 0° C. to about 90° C., preferably from about 20° C. to about 70° C., more preferably from about 40° C. to about 50° C. and agitated for about 4 hours or until the reaction is complete to yield a compound of formula I or salts thereof. A preferred salt of the compound of formula I is the following:

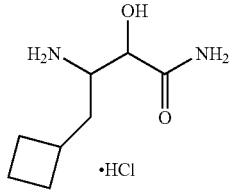

The following non-limiting EXAMPLES are provided in order to further illustrate the present invention. It will be apparent to those skilled in the art that many modifications, variations and alterations to the present disclosure, both to materials, methods and reaction conditions, may be practiced. All such modifications, variations and alterations are intended to be within the spirit and scope of the present invention

EXAMPLES

Unless otherwise stated, the following abbreviations have the stated meanings in the Examples below:
MHz=Megahertz
NMR=nuclear magnetic resonance spectroscopy
mL=milliliters
g=grams
THF=tetrahydrofuran
TFA=trifluoroacetic acid
TEMPO=2,2,6,6-Tetramethyl-1-piperidinyloxy
DMSO=dimethylsulfoxide
TBME=t-butylmethyl ether
t-Boc=t-butyl carbonate

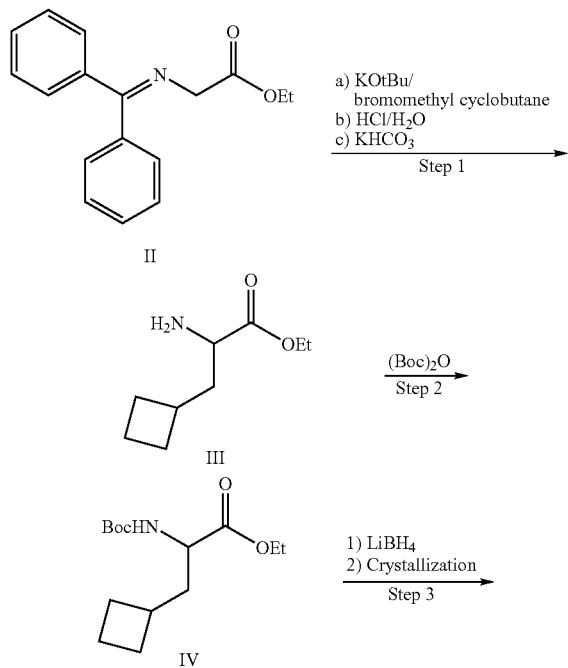

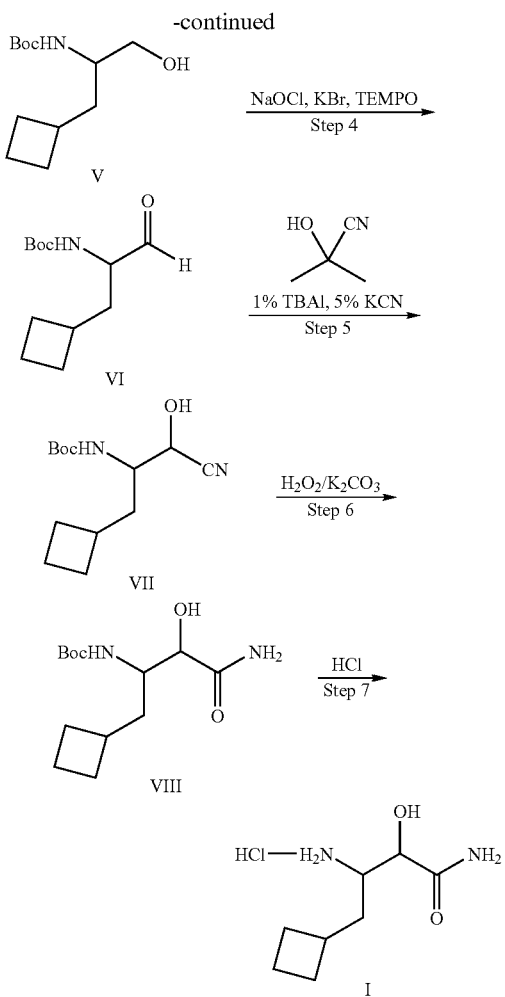

Step 1:
To a solution of 35.0 kg (131 mol) of (diphenylmethylene) glycine ethyl ester II in 158 L of THF at −20° C. to −30° C. was added a solution of 17.9 kg (160 mol) of potassium tert-butoxide in 158 L of THF. After the addition, the mixture was warmed to −5° C. to 0° C. and agitated for 1 hour, and 18 L (162 mol) of (bromomethyl)cyclobutane was added. After the addition, the mixture was further warmed to 20° C. to 25° C. and agitated for 24 hours. After this period of time, a solution of 35 L of HCl (37% in 140 L of water) was added. The resulting mixture was agitated for 2 hours, then settled, and separated. Organic layer was washed with 105 L of water. Aqueous layers were combined and washed with 280 L of TBME twice. After washes, to the aqueous layer was added 175 L of TBME and a solution of 52.5 kg of potassium carbonate in 105 L of water. The resulting mixture was agitated for 30 minutes, settled, and separated. The aqueous layer was extracted with 175 L of TBME to yield an organic layer containing the compound of formula III.

Step 2:
The combined organic layer from step 1 was concentrated to a volume of 140 L and cooled to 0° C. to 5° C. Di-tert-butyldicarbonate (75% wt. solution in THF) (24.9 kg, 131 mol) was added. After the addition, the mixture was warmed to 20° C. to 25° C., agitated for 4 hours, and washed with 70 L of water. The organic layer was dried via azeotropic distillation, concentrated to a volume of 140 L, and cooled to 30° C. to 35° C. to yield the compound of formula IV.

Step 3:

A solution of lithium borohydride in THF (2.0M) (58.5 kg, 131 mol) was added to the compound of formula IV from step 2. The resulting mixture was agitated for 6 hours and cooled to 15° C. to 20° C. The reaction was quenched by addition of a solution of 17.5 kg of potassium dihydrogen phosphate in 175 L of water. After separation, the aqueous layer was extracted with 105 L of TBME. The combined organic layers were washed with water and sodium chloride solution. TBME in organic layer was displaced with heptane via distillation and the product was crystallized from the heptane solution. After filtration and drying, 13.0 kg of the compound of formula V (43%) was obtained.

1H NMR 400 MHz (CDCl3): δ 4.7 (1H), 3.6 (2H), 3.5 (1H), 2.8 (1H), 2.4 (1H), 2.1 (2H), 1.9 (2H), 1.7 (2H), 1.6 (2H), and 1.5 (9H).

Step 4:

To a solution of 100.0 g (0.436 mole) of the compound of formula V from step 3 and TEMPO (1.0 g, 6.4 mmole) in ethyl acetate (1.0 L) was added a solution of lithium bromide (3.0 g, 34.5 mmole) and sodium bicarbonate (30 g, 0.357 mole) in water (500 ml). The mixture was cooled to −5 to 5° C. Sodium hypochlorite solution 15% (197.3 ml, 0.436 mole) was added over 2 hours. After addition, the reaction mixture was stirred for 30 minutes. Upon reaction completion, sodium thiosulfate (20 g, 80.6 mmole) was added, then the aqueous layer was separated to yield an ethyl acetate layer containing the compound of formula VI.

Step 5:

To the ethyl acetate layer from step 4 were added tetrabutylammonium iodide (1.0 g, 2.7 mmole) and potassium cyanide (4.0 g, 61.4 mmole) in water (50 ml). At 15° C. to 25° C., acetone cyanohydrin (51.0 g, 0.599 mole) was added. The mixture was stirred for 2 hours. Upon reaction completion, the aqueous layer was separated. Organic layer was then washed with 20% sodium chloride solution (350 ml) and concentrated to yield an ethyl acetate layer containing the compound of formula VII.

Step 6:

The ethyl acetate in the organic layer in step 5 was displaced with DMSO (250 ml) via distillation. Potassium carbonate (40 g, 0.289 mole) and acetone (700 ml) were added. The mixture was heated to reflux at about 65° C. At reflux, 30% hydrogen peroxide (100 ml, 0.979 mole) was added over 2 hours. Then the reaction mixture was stirred at reflux for 3 hours. Upon reaction completion, water (800 ml) was added at 35° C. to 45° C. The product precipitated during the addition. The mixture was cooled to 0° C. to 5° C. and filtered to give the product, designated as PART 1, which was predominantly either the RR or SS isomer. $^1$H NMR 400 MHz (CDCl$_3$): δ 6.82 (s, 1H), 5.64 (s, 1H), 5.2 (m, 1H), 4.90 (d, J=8 Hz, 1H), 4.21 (d, J=1.76 Hz, 1H), 3.72 (m, 1H), 2.37 (m, 1H), 2.07 (m, 2H), 1.86 (m, 3H), 1.66 (m, 3H), 1.43 (s, 9H).

Acetone in the filtrate was removed through vacuum distillation. Ethyl acetate (1.2 L) was added to extract the product. The ethyl acetate extract was washed in sequence with water twice and sodium chloride solution. Ethyl acetate was removed through vacuum distillation. The rest of ethyl acetate was displaced with n-butyl acetate through vacuum distillation. The product, PART 2, precipitated from butyl acetate and was collected through filtration. This was predominantly either the RS or SR isomer. $^1$H NMR 400 MHz (CDCl$_3$): δ 6.87 (s, 1H), 5.78 (s, 1H), 5.19 (d, J=7.6 Hz, 1H), 4.09 (d, J=2.30 Hz, 1H), 3.72 (m, 1H), 2.36 (m, 1H), 2.08 (m, 2H), 1.88 (m, 3H), 1.68 (m, 3H), 1.45 (s, 9H).

A total of 80 g (67.4%) of the combined PART 1 and PART 2 of the compound of formula VIII was obtained.

Step 7:

To a mixture of 15.0 kg (55.1 mol) of the compound of formula VIII from step 6 in 135 L of isopropyl alcohol at 20° C. to 25° C. was added 30 L of 5-6N HCl in isopropyl alcohol. After the addition, the mixture was heated to 40° C. to 50° C. and agitated for 4 hours. After this period of time, the mixture was cooled to 0° C. to 5° C. and filtered. The wet cake was dried to give 10.9 kg of the hydrochloride salt of the compound of the formula I (91%).

1H NMR 400 MHz (DMSO): δ 4.2 and 4.0 (1H), 3.3 and 3.1 (1H), 2.4 (1H), 2.0 (2H), 1.8 (2H), and 1.6 (4H).

It will be understood that various modifications can be made to the embodiments and examples disclosed herein. Therefore, the above description should not be construed as limiting, but merely as exemplifications of preferred embodiments. Those skilled in the art will envision various modifications within the scope and spirit of the claims appended hereto.

What is claimed is:

1. A reaction mixture precipitate comprising predominantly the RR and SS enantiomer of Formula VIII;

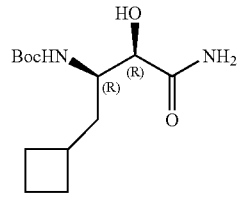

Formula VIII RR

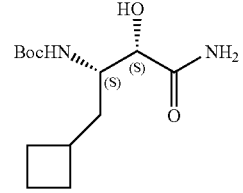

Formula VIII SS wherein the precipitate is prepared by a process comprising:
(a) providing a reaction mixture by treating a DMSO solution of the compound of VII,

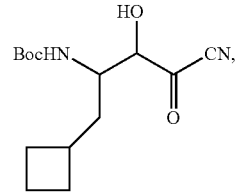

VII with a base in a suitable solvent and subsequently reacting it with peroxide; and
(b) precipitating the compounds of VIII RR and SS by adding an anti-solvent to the reaction mixture provided by step "a".

2. The precipitate of claim 1 prepared by the process comprising:

a) reacting the compound of formula VI with

to yield a compound of formula VII:

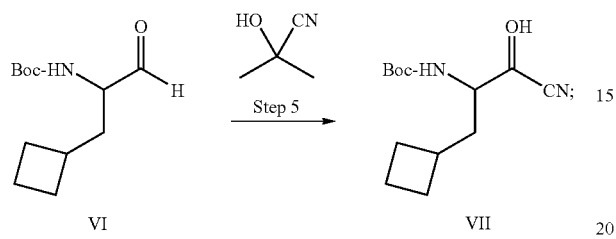

b) hydrating the compound of formula VII in a reaction mixture comprising a low polarity solvent to yield a compound of formula VIII:

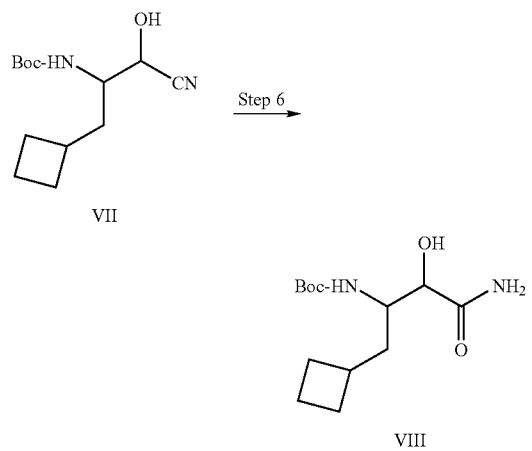

c) precipitating the RR and SS enantiomer of the compound of Formula VIII by adding water to the reaction mixture from step "b".

3. A reaction mixture precipitate comprising predominantly the RS and SR enantiomer of Formula VIII;

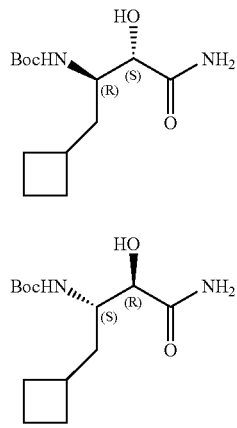

Formula VIII RS Formula VIII SR wherein the precipitate is prepared by a process comprising:

(a) separating the precipitate formed in Step "b" of claim 1 from the supernatant liquid by filtration;

(b) extracting the compounds of Formula VIII RS and VIII SR into ethylacetate;

(c) displacing the ethylacetate in the extract formed in Step "b" with n-butylacetate to form a butyl acetate solution comprising predominantly compounds of Formula VIII RS and VIII SR; and (d) precipitating the compounds of compounds of Formula VIII RS and VIII SR from the butyl acetate solution provided in Step "c".

* * * * *